United States Patent [19]

Berges

[11] 4,171,368
[45] Oct. 16, 1979

[54] 7-ACYLAMINO-3-(SULFAMINOALKYL SUBSTITUTED TETRAZOLYLTHIOMETHYL)CEPHALOSPORINS, ANTIBACTERIAL COMPOSITIONS CONTAINING THEM AND METHODS OF TREATING BACTERIAL INFECTIONS WITH THEM

[75] Inventor: David A. Berges, Wayne, Pa.

[73] Assignee: SmithKline Corporation, Philadelphia, Pa.

[21] Appl. No.: 924,522

[22] Filed: Jul. 14, 1978

Related U.S. Application Data

[60] Division of Ser. No. 704,142, Jul. 12, 1976, Pat. No. 4,118,491, which is a continuation-in-part of Ser. No. 665,837, Mar. 11, 1976, abandoned, which is a continuation-in-part of Ser. No. 627,164, Oct. 30, 1975, abandoned.

[51] Int. Cl.² .............. A61K 31/545; C07D 501/50; C07D 501/52; C07D 501/56
[52] U.S. Cl. .................................... 424/246; 544/21; 544/26; 544/27
[58] Field of Search ............... 424/246; 544/21, 26, 544/27

[56] References Cited

U.S. PATENT DOCUMENTS

| 3,929,779 | 12/1975 | Bickel et al. | 544/27 |
|---|---|---|---|
| 3,931,160 | 1/1976 | Dunn | 544/26 |
| 4,039,536 | 8/1977 | Takano et al. | 544/27 X |
| 4,066,762 | 1/1978 | Dunn | 544/27 X |
| 4,068,074 | 1/1978 | Murakami et al. | 544/27 |
| 4,077,965 | 3/1978 | Kamiya et al. | 544/26 X |
| 4,101,656 | 7/1978 | Berges | 424/246 |
| 4,110,338 | 8/1978 | Kamiya et al. | 424/246 X |
| 4,117,123 | 9/1978 | Berges | 424/246 |

FOREIGN PATENT DOCUMENTS 2415402 10/1974 Fed. Rep. of Germany ............ 544/26

Primary Examiner—Donald G. Daus
Assistant Examiner—Diana G. Rivers
Attorney, Agent, or Firm—Janice E. Williams; William H. Edgerton; Alan D. Lourie

[57] ABSTRACT

The compounds of this invention are cephalosporins having various acyl substituents at the 7-position and a sulfaminoalkyl substituted tetrazolylthiomethyl group at the 3-position of the cephem nucleus and intermediates for the preparation thereof. The 7-acylated cephalosporin compounds have antibacterial activity.

21 Claims, No Drawings

7-ACYLAMINO-3-(SULFAMINOALKYL SUBSTITUTED TETRAZOLYLTHIOMETHYL)CEPHALOSPORINS, ANTIBACTERIAL COMPOSITIONS CONTAINING THEM AND METHODS OF TREATING BACTERIAL INFECTIONS WITH THEM

This application is a divisional of application Ser. No. 704,142, filed July 12, 1976, now U.S. Pat. No. 4,118,491, which is a continuation-in-part of application Ser. No. 665,837, filed Mar. 11, 1976, now abandoned, which is continuation-in-part of application Ser. No. 627,164, filed Oct. 30, 1975, now abandoned.

This invention relates to a new series of cephalosporin compounds which have antibacterial activity when administered parenterally and to intermediates for the preparation thereof. In particular, the structures of the biologically active cephalosporin compounds of this invention are characterized by having a sulfaminoalkyl substituted tetrazolylthiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

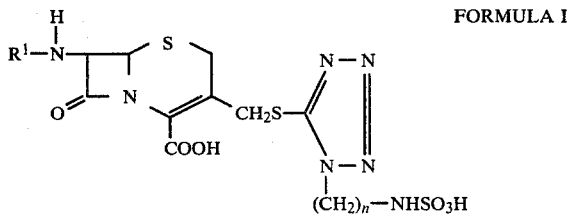

FORMULA I in which:

$R^1$ is an acyl group selected from the group consisting of:

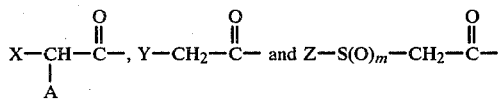

where:

X is thienyl, dihydrophenyl, phenyl or phenyl monosubstituted with hydroxy, hydroxymethyl, formamido, ureido or carboxymethylamino;

A is $NH_2$, OH, COOH or $SO_3H$; or formyloxy when X is phenyl;

Y is thienyl, tetrazolyl, sydnone, cyano or aminomethylphenyl;

Z is methyl, trifluoromethyl, trifluoroethyl, cyanomethyl or pyridyl;

m is zero to two; and n is two to five, or a non-toxic pharmaceutically acceptable salt thereof.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

A selected group of compounds of this invention is represented by Formula I where n is two.

Another group of compounds of this invention is represented by Formula I where n is two, X is phenyl, A is $NH_2$ or OH, Y is thienyl or tetrazolyl, Z is trifluoromethyl and m is zero.

Examples of representative 7-acyl substituents ($R^1NH$) of the compounds of Formula I are listed below:

α-hydroxyphenylacetamido
α-aminophenylacetamido
α-amino-4-hydroxyphenylacetamido
trifluoromethylthioacetamido
methylthioacetamido
α-carboxythienylacetamido
α-carboxyphenylacetamido
α-sulfophenylacetamido
α-amino-4-carboxymethylaminophenylacetamido
2-aminomethylphenylacetamido
3-sydnoneacetamido
tetrazolylacetamido
thienylacetamido
2,2,2-trifluoroethylsulfinylacetamido
cyanoacetamido
methylsulfonylacetamido
cyanomethylthioacetamido
4-pyridylthioacetamido
2-pyridoneacetamido
4-pyridoneacetamido.

Some examples of the compounds of Formula I are 7-D-mandelamido-3-[1-(2-sulfaminoethyl)tetrazol-5-ylthiomethyl]-3-cephem-4-carboxylic acid, 7-(2-thienylacetamido)-3-[1-(2-sulfaminoethyl)tetrazol-5-ylthiomethyl]-3-cephem-4-carboxylic acid, 7-(1-tetrazolylacetamido)-3-[1-(2-sulfaminoethyl)tetrazol-5-ylthiomethyl]-3-cephem-4-carboxylic acid and 7-trifluoromethylthioacetamido-3-[1-(2-sulfaminoethyl)tetrazol-5-ylthiomethyl]-3-cephem-4-carboxylic acid.

Cephalosporin derivatives having 7-acyl substituents as defined above are well documented in the prior art. Although substitution by variously substituted S-heterocyclicthiomethyl groups ($—CH_2SHet$) at the 3-position of the cephem nucleus is also known, no compounds containing the 3-(sulfaminoalkyl substituted tetrazolyl)thiomethyl moiety disclosed herein are believed to be known to the art.

The compounds of Formula I are prepared by acylating 7-aminocephalosporanic acid with an appropriately protected acylating agent and then displacing the 3-acetoxy group with the desired sulfaminoalkyltetrazole thiol or its corresponding salt with subsequent removal of the protective group(s) when present. The carboxylic acid group of the acylating agent is activated by any of the standard methods such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-methoxybenzyl or p-nitrobenzyl ester. When A is $NH_2$, the α- amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

The sulfaminoalkyltetrazole thiols of the formula:

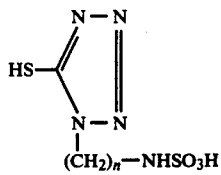

FORMULA II in which n is two to five,
are also objects of this invention, being important intermediates for producing pharmaceutical end products as described herein.

Alternatively, the compounds of Formula I are prepared by acylation of an appropriate 7-amino-3-sulfaminoalkyltetrazolylthiomethyl cephalosporin nucleus of Formula III:

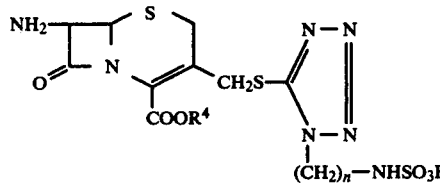

FORMULA III in which:
n is two to five; and
$R^4$ is hydrogen or a protecting ester group,
with an appropriate acylating agent followed by removal of the protective groups when present.

The compounds of Formula III above are also considered as objects of this invention.

The protective groups can be removed according to methods well known to the art, such as with trifluoroacetic acid when t-butyl or t-butoxycarbonyl protective groups are used. The resulting salt is converted to the zwitterionic product or to the free acid by means of an ion exchange resin such as polystyrene-amine ion exchange resin (Amberlite IR-45) or else by basification of an aqueous solution of the salt.

The acylating agents used as starting materials are either known or prepared by known methods.

The 7-amino-3-sulfaminoalkyltetrazolylthiomethyl cephalosporin starting materials of Formula III are prepared from reaction of 7-formamidocephalosporanic acid, prepared by reaction of 7-aminocephalosporanic acid with formic acid and acetic anhydride, and a substituted tetrazole thiol of Formula II followed by treatment with acid such as hydrochloric acid to remove the formyl group.

The sulfaminoalkyltetrazole thiols of Formula II are prepared by reaction of the corresponding 1-aminoalkyl-5-(2,4-dinitrophenylthio)tetrazole compounds, prepared from 2,4-dinitrofluorobenzene and a 1-acetamidoalkyltetrazole-5-thiol followed by acid hydrolysis of the acetamido moiety, with sulfur trioxide-trimethylamine complex with subsequent cleavage of the 2,4-dinitrophenyl protecting group. The 1-acetamidoalkyltetrazole-5-thiols are prepared by reaction of an acetamidoalkyldithiocarbamate such as methyl 2-acetamidoethyldithiocarbamate with an azide such as sodium azide. The acetamidoalkyldithiocarbamates are prepared by treatment of a N-aminoalkylacetamide such as N-(2-aminoethyl)acetamide with carbon disulfide and an alkyl halide such as methyl iodide in the presence of a base such as triethylamine.

Certain compounds of this invention are capable of forming salts with, for example, the alkali metals such as sodium or potassium, the alkaline earth metals such as calcium or with the ammonium cation. When A of Formula I is $NH_2$, the compounds can exist as the zwitterion or as either an acid or base salt. These salts are prepared by standard methods using a wide variety of non-toxic pharmaceutically acceptable acids and bases known in the art. Salts of the compounds of Formulas I, II and III are considered as objects of this invention.

It will be recognized that due to the asymmetric α-carbon atom in the 7-acetamido group of Formula I when $R^1$ is

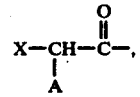

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have antibacterial activity against both Gram-positive and Gram-negative organisms. Minimum inhibitory concentrations (MIC's) range from 0.2 to >200 µg/ml in in vitro testing. Test results for representative compounds are given in Table 1 below. In vivo mouse protection data ($ED_{50}$'s) is given in Table 2. Names corresponding to compound numbers are given in Table 3.

TABLE 1

| | MIC (µg/ml) in vitro | | | |
| | Compound Number | | | |
| Bacteria | 1 | 2 | 3 | 4 |
|---|---|---|---|---|
| S. aureus HH 127 | 3.1, 3.1 | 1.6 | 3.1 | 1.6 |
| S. aureus SK 23390 | 0.8, 0.8 | 0.4 | 3.1 | 1.6 |
| S. villaluz SK 70390 | 50, 200 | 25 | >200 | >200 |
| Strep. faecalis HH 34358 | 100, 50 | 12.5 | 50 | 100 |
| E. coli SK 12140 | 0.8, 0.8 | 3.1 | 0.8 | 0.8 |
| E. coli HH 3377 | 3.1, 1.6 | 12.5 | 0.8 | 1.6 |
| Kleb. pneumo. SK 4200 | 1.6, 0.8 | 3.1 | 0.8 | 0.8 |
| Kleb. pneumo. SK 1200 | 0.4, 0.2 | 0.8 | 0.4 | 0.2 |
| Salmonella ATCC 12176 | 0.2, 1.6 | 12.5 | 0.4 | 0.4 |

TABLE 1-continued

| Bacteria | MIC (μg/ml) in vitro Compound Number | | | |
|---|---|---|---|---|
| | 1 | 2 | 3 | 4 |
| *Shigella* HH 117 | 0.4, 0.2 | — | 0.4 | 0.8 |
| *Pseudo. aerug.* HH 63 | >200, >200 | >200 | >200 | >200 |
| *Serratia marc.* ATCC 13880 | 100, 100 | >200 | 200 | 100 |
| *Proteus morgani* 179 | 1.6, 3.1 | >200 | 200 | >200 |
| *Entero. aerog.* ATCC 13048 | 50, 6.3 | 25 | 3.1 | 6.3 |
| *Entero. cloacae* HH 31254 | 1.6, 1.6 | 6.3 | 0.8 | 1.6 |

TABLE 2

| Compound Number | ED₅₀ (mg/kg) in vivo | | | |
|---|---|---|---|---|
| | *E. coli* SK 12140 | | *Kleb. pneumo.* SK 4200 | |
| | s.c. | p.o | s.c. | p.o. |
| 1 | 0.46 | 50 | 0.46 | — |
| 2 | 1.02 | >50 | — | — |
| 3 | 1.56 | — | — | — |
| 4 | 1.82 | 50 | — | — |

TABLE 3

| Compound Number | Compound Name |
|---|---|
| 1 | 7-D-mandelamido-3-[1-(2-sulfaminoethyl)tetrazol-5-ylthiomethyl]-3-cephem-4-carboxylic acid |
| 2 | 7-(2-thienylacetamido)-3-[1-(2-sulfaminoethyl)tetrazol-5-ylthiomethyl]-3-cephem-4-carboxylic acid |
| 3 | 7-(1-tetrazolylacetamido)-3-[1-(2-sulfaminoethyl)tetrazol-5-ylthiomethyl]-3-cephem-4-carboxylic acid |
| 4 | 7-trifluoromethylthioacetamido-3-[1-(2-sulfaminoethyl)tetrazol-5-ylthiomethyl]-3-cephem-4-carboxylic acid |

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be by parenteral injection such as subcutaneously, intramuscularly or intravenously. The injection of suitably prepared sterile solutions or suspensions containing an effective, non-toxic amount of the new cephalosporin compound is the preferred route of administration.

The compounds of Formula I are formulated and administered in the same manner as other cephalosporins. The dosage regimen comprises administration, preferably by injection, of an active but non-toxic quantity of a compound of Formula I selected from the dosage unit range of from 100 to 1000 mg with the total daily dosage regimen being from 400 mg to 6 g. The precise dosages are dependent upon the age and weight of the subject and on the infection being treated and can be determined by those skilled in the art based on the data disclosed herein compared with that available to the art attained with known cephalosporins.

Also considered within the scope of this invention are the 7α-methoxy analogs of the compounds of Formula I, which compounds are represented by the following structural formula:

FORMULA IV

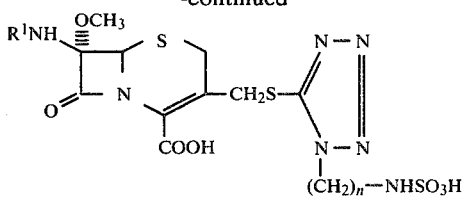

or a non-toxic pharmaceutically acceptable salt thereof, in which $R^1$ and n are as previously defined hereabove.

A selected group of the compounds of Formula IV are those where n is two.

Representative of the compounds of Formula IV are 7α-methoxy-7β-(2-thienylacetamido)-3-[1-(2-sulfaminoethyl)tetrazol-5-ylthiomethyl]-3-cephem-4-carboxylic acid, 7α-methoxy-7β-trifluoromethylthioacetamido-3-[1-(2-sulfaminoethyl)tetrazol-5-ylthiomethyl]-3-cephem-4-carboxylic acid, 7β-D-mandelamido-7α-methoxy-3-[1-(2-sulfaminoethyl)tetrazol-5-ylthiomethyl]-3-cephem-4-carboxylic acid and 7α-methoxy-7β-(1-tetrazolylacetamido)-3-[1-(2-sulfaminoethyl)tetrazol-5-ylthiomethyl]-3-cephem-4-carboxylic acid.

The compounds of Formula IV are preferably prepared by displacing the 3-acetoxy group from a 7α-methoxy-7β-acylaminocephalosporanic acid or salt thereof, suitably protected as necessary, with a substituted tetrazole thiol of Formula II, or a corresponding salt, with subsequent removal of the protective group(s), and conversion of any salts to the corresponding free acids, all as described hereinabove. The 7α-methoxy-7β-acylaminocephalosporanic acids or salts are either known to the art or are prepared by known methods.

As with the compounds of Formula I, all non-toxic pharmaceutically acceptable salts and all isomers, including separated isomers and mixtures thereof, of the compounds represented by Formula IV are included within the scope of this invention.

The compounds of Formula IV have anti-bacterial activity against both Gram-positive and Gram-negative organisms. They are administered and formulated in the same manner as previously described for the compounds of Formula I.

The following examples illustrate the invention but are not to be construed as limiting the scope thereof. Temperatures are in degrees Centigrade (°C.) unless otherwise stated.

EXAMPLE 1

7-D-Mandelamido-3-[1-(2-sulfaminoethyl)tetrazol-5-ylthiomethyl]-3-cephem-4-carboxylic acid To a solution of 20.4 g (0.20 mol) of N-(2-aminoethyl)acetamide in 200 ml of 95% ethanol was added 27.9 ml (0.20 mol) of triethylamine and 12.0 ml (0.20 mol) of carbon disulfide. The exothermic reaction reached reflux and then cooled to ambient temperature over a 1.5 hour period. Methyl iodide (28.4 g, 0.20 mol) was added which again produced an exothermic reaction. After 1.75 hours the reaction mixture was evaporated to dryness and the solid residue was dissolved in 200 ml of water. The aqueous solution was extracted twice with 250 ml portions of ethyl acetate. The extracts were combined, shaken with sodium thiosulfate, dried (MgSO$_4$) and evaporated to dryness to give methyl 2-acetamidoethyldithiocarbamate.

To a solution of 38.4 g (0.198 mol) of methyl 2-acetamidoethyldithiocarbamate in 100 ml of 95% ethanol was added a solution of 13.5 g (0.208 mol) of sodium azide in 100 ml of water. The reaction mixture was refluxed for 24 hours then cooled and concentrated under reduced pressure to about half volume. The solution was cooled to 15° and 50 ml of 6 N sulfuric acid was added. The acidic solution was filtered and the filtrate was concentrated to about 100 ml and chilled at 5° to induce crystallization of 1-(2-acetamidoethyl)tetrazole-5-thiol which was collected by filtration, mp 139°–139.5°. Additional amounts of the product were obtained by continuous extraction of the filtrate with ethyl acetate.

A solution of 9.3 g (0.050 mol) of 2,4-dinitrofluorobenzene in 50 ml of acetone was added to a solution of 9.35 g (0.050 mol) of 1-(2-acetamidoethyl)tetrazole-5-thiol and 6.85 ml (0.050 mol) of triethylamine in 100 ml of acetone and the reaction mixture was stirred for 1 hour. The solid material was collected by filtration and recrystallized from acetonitrile to give 1-(2-acetamidoethyl)-5-(2,4-dinitrophenylthio)tetrazole, mp 197°–198°.

A mixture of 6.5 g (0.02 mol) of 1-(2-acetamidoethyl)-5-(2,4-dinitrophenylthio)tetrazole, 100 ml of 12 N hydrochloric acid and 100 ml of 95% ethanol was refluxed for 4.5 hours. The mixture was evaporated to dryness to give a gummy residue which crystallized upon addition of ethanol to give 1-(2-aminoethyl)-5-(2,4-dinitrophenylthio)tetrazole hydrochloride, mp 217°–219° (d).

To a solution of 3.5 g (0.01 mol) of 1-(2-aminoethyl)-5-(2,4-dinitrophenylthio)tetrazole hydrochloride in 30 ml of dry dimethylformamide was added 1.4 g (0.01 mol) of sulfur trioxide-trimethylamine complex followed by 1.4 ml (0.01 mol) of triethylamine. The mixture was stirred for 0.5 hour and then filtered. The filtrate was evaporated in vacuo, acetone was added to the residue, the precipitate was removed by filtration and the filtrate was evaporated to dryness. Methanol was added to the residue and the solid material produced upon scratching was removed by filtration. The methanolic filtrate was brought to pH 11.3 by addition of 5% methanolic sodium methoxide, stirred for 1.25 hours, filtered and diluted with 300 ml of ether. The resulting solid was removed by filtration and the filtrate was evaporated to dryness to give a residue which was triturated with 95% ethanol to induce crystallization. The solid product was collected by filtration and dissolved in methanol and the methanolic solution was concentrated to 10 ml, diluted with 75 ml of 95% ethanol and re-concentrated to 5 ml to give 1-(2-sulfaminoethyl)tetrazole-5-thiol disodium salt, mp 122°–127°.

$C_3H_5N_5O_3S_2.2Na.1.5H_2O$: Calculated: 12.16% C; 2.72% H; 23.64% N. Found: 12.25% C; 2.98% H; 23.77% N.

A solution of 1-(2-sulfaminoethyl)tetrazole-5-thiol disodium salt in water is passed through an Amberlite IR-120H ion exchange resin column to give, after lyophilization, 1-(2-sulfaminoethyl)tetrazole-5-thiol.

To a mixture of 2.71 g (0.006 mol) of 7-D-mandelamidocephalosporanic acid sodium salt and 1.18 g (0.004 mol) of 1-(2-sulfaminoethyl)tetrazole-5-thiol disodium salt in 30 ml of water was added 10% aqueous sodium hydroxide solution and then 5% aqueous sodium bicarbonate solution to pH 7.3. The reaction mixture was heated at 70° for 2–6 hours, then it was cooled, covered with ethyl acetate, acidified to pH 2.5 with 3 N hydrochloric acid and extracted twice with ethyl acetate. The aqueous phase was neutralized to pH 7.0 by addition of 10% aqueous sodium hydroxide and then 5% aqueous sodium bicarbonate solutions and chromatographed on XAD-7 resin with water and methanol as eluants. After removing the methanol in vacuo the chromatography fractions were lyophilized to give 7-D-mandelamido-3-[1-(2-sulfaminoethyl)tetrazol-5-ylthiomethyl]-3-cephem-4-carboxylic acid disodium salt.

$C_{19}H_{19}N_7O_8S_3.2Na.3H_2O$: Calculated: 34.08% C; 3.76% H; 14.64% N. Found: 34.56% C; 3.25% H; 13.96% N.

An aqueous solution of 7-D-mandelamido-3-[1-(2-sulfaminoethyl)tetrazol-5-ylthiomethyl]-3-cephem-4-carboxylic acid disodium salt is passed through a column of Amberlite IR-120H ion exchange resin to give the title compound.

EXAMPLE 2

7-(2-Thienylacetamido)-3-[1-(2-sulfaminoethyl)tetrazole-5-ylthiomethyl]-3-cephem-4-carboxylic acid A mixture of 1.89 g (0.064 mol) of 1-(2-sulfaminoethyl)tetrazole-5-thiol disodium salt and 2.67 g (0.064 mol) of 7-(2-thienylacetamido)cephalosporanic acid sodium salt in 40 ml of water was heated at 69° for 5.5 hours while maintaining the pH at 7.4 by addition of dilute aqueous sodium bicarbonate solution. After cooling, the mixture was extracted with ethyl acetate. The aqueous phase was neutralized, evaporated to dryness and the residue was passed through a XAD-4 column eluting with water and methanol. The methanol was removed by evaporation and the aqueous residue was lyophilized to give a solid material. The solid was suspended in methanol, the insoluble material was removed by filtration and the filtrate was evaporated to dryness to give 7-(2-thienylacetamido)-3-[1-(2-sulfaminoethyl)tetrazol-5-ylthiomethyl]-3-cephem-4-carboxylic acid disodium salt.

$C_{17}H_{17}N_7O_7S_4.2Na.1CH_4O$: Calculated: 33.90% C; 3.31% H; 15.37% N. Found: 34.04% C; 3.57% H; 14.74% N.

7-(2-Thienylacetamido)-3-[1-(2-sulfaminoethyl)tetrazol-5-yl-thiomethyl]-3-cephem-4-carboxylic acid disodium salt is converted to the title compound as described in Example 1.

EXAMPLE 3

7-(1-Tetrazolylacetamido)-3-[1-(2-sulfaminoethyl)tetrazole-5-ylthiomethyl]-3-cephem-4-carboxylic acid A mixture of 3.5 g (8.5 mmol) of 7-(1-tetrazolylacetamido)cephalosporanic acid sodium salt and 2.96 g (10 mmol) of 1-(2-sulfaminoethyl)tetrazole-5-thiol disodium salt in 50 ml of water was stirred at 65° for 6.5 hours while maintaining the pH of the reaction mixture at 7.0 by addition of 5% aqueous sodium bicarbonate solution. The mixture was cooled to ambient temperature, acidified to pH 1.5 with 3 N hydrochloric acid, filtered and extracted three times with ethyl acetate. The pH of the aqueous phase was then adjusted to 7.0 by addition of sodium bicarbonate, the solution was chromatographed on a XAD-2 column and the resulting product was freeze-dried to give 7-(1-tetrazolylacetamido)-3-[1-(2-sulfaminoethyl)tetrazol-5-ylthiomethyl]-3-cephem-4-carboxylic acid disodium salt.

$C_{14}H_{15}N_{11}O_7S_3.2Na.2H_2O$: Calculated: 26.80% C; 3.37% H; 24.55% N. Found: 27.11% C; 3.40% H; 24.18% N.

7-(1-Tetrazolylacetamido)-3-[1-(2-sulfaminoethyl)tetrazol-5-ylthiomethyl]-3-cephem-4-carboxylic acid disodium salt is converted to the title compound as described in Example 1.

EXAMPLE 4

7-Trifluoromethylthioacetamido-3-[1-(2-sulfaminoethyl)tetrazol-5-ylthiomethyl]-3-cephem-4-carboxylic acid A solution of 3.05 g (0.01 mol) of 1-(2-sulfaminoethyl)tetrazole-5-thiol disodium salt and 4.36 g (0.01 mol) of 7-trifluoromethylthioacetamidocephalosporanic acid sodium salt in 50 ml of water was heated at 70° for 5.5 hours while maintaining the pH at 7.5 with 5% aqueous sodium bicarbonate. The reaction mixture was diluted with 50 ml of water and extracted twice with ethyl acetate. The aqueous phase was acidified to pH 2 and extracted three times with ethyl acetate. The aqueous layer was brought to pH 7.4 by addition of 5% aqueous sodium bicarbonate and the solution was passed through a XAD-4 resin column while eluting with water followed by methanol. The methanol solution was evaporated to dryness and the residue was dissolved in 75 ml of water. The aqueous solution was extracted twice with ether and petroleum ether then lyophilized. The lyophilized material was dissolved in methanol, the solvent was evaporated to dryness and triturated with ether to give 7-trifluoromethylthioacetamido-3-[1-(2-sulfaminoethyl)tetrazol-5-ylthiomethyl]-3-cephem-4-carboxylic acid disodium salt.

$C_{14}H_{14}F_3N_7O_7S_4.2Na.2H_2O$: Calculated: 25.49% C; 2.75% H; 14.86% N. Found: 25.85% C; 2.78% H; 14.13% N.

7-Trifluoromethylthioacetamido-3-[1-(2-sulfaminoethyl)tetrazol-5-ylthiomethyl]-3-cephem-4-carboxylic acid disodium salt is converted to the title compound as described in Example 1.

EXAMPLE 5

7-(D-α-Aminophenylacetamido)-3-[1-(2-sulfaminoethyl)tetrazol-5-ylthiomethyl]-3-cephem-4-carboxylic acid A solution of 7.58 g (0.015 mol) of 7-(D-α-t-butoxycarbonylaminophenylacetamido)cephalosporanic acid, 2.96 g (0.01 mol) of 1-(2-sulfaminoethyl)tetrazole-5-thiol disodium salt and 1.26 g (0.015 mol) of sodium bicarbonate in 125 ml of water is stirred at 60° for 5 hours while maintaining the pH at 7.0-7.2 by addition of sodium bicarbonate. The mixture is cooled and extracted with ethyl acetate. The aqueous phase is acidified to pH 2.5 with 3 N hydrochloric acid and the acidic solution is extracted again with ethyl acetate. The aqueous phase is brought to pH 7.1 by addition of 5% sodium carbonate solution, then passed through a XAD-4 ion exchange resin column and eluted with water and methanol to give 7-(D-α-t-butoxycarbonylaminophenylacetamido)-3-[1-(2-sulfaminoethyl)tetrazol-5-ylthiomethyl]-3-cephem-4-carboxylic acid disodium salt.

7-(D-α-t-Butoxycarbonylaminophenylacetamido)-3-[1-(2-sulfaminoethyl)tetrazol-5-ylthiomethyl]-3-cephem-4-carboxylic acid disodium salt is stirred at 25° with 25 ml of trifluoroacetic acid and 25 ml of 1,3-dimethoxybenzene for 2.25 hours. The mixture is evaporated to dryness, ether is added to the residue and the precipitate is collected, washed with ether, stirred in acetonitrile for 2 hours and dried in vacuo to give the title compound as the trifluoroacetic acid salt.

An aqueous solution of the trifluoroacetic acid salt is brought to pH 5.0 by addition of dilute aqueous sodium hydroxide. After lyophilization, the lyophilized material is dissolved in methanol and ether is added to precipitate 7-(D-α-aminophenylacetamido)-3-[1-(2-sulfaminoethyl)tetrazol-5-ylthiomethyl]-3-cephem-4-carboxylic acid sodium salt. The sodium salt is dissolved in water and the aqueous solution is passed through an Amberlite IR-120H ion exchange resin column. Lyophilization of the eluted material gives the title compound.

EXAMPLE 6

Reaction of the N-t-butoxycarbonyl derivative of the following cephalosporanic acids:

7-(α-amino-4-hydroxyphenylacetamido)cephalosporanic acid 7-(α-amino-4-formamidophenylacetamido)cephalosporanic acid 7-(α-amino-3-formamidophenylacetamido)cephalosporanic acid 7-(α-amino-4-ureidophenylacetamido)cephalosporanic acid 7-(α-amino-3-ureidophenylacetamido)cephalosporanic acid 7-(α-amino-4-hydroxymethlyphenylacetamido)cephalosporanic acid 7-(α-amino-1,4-cyclohexadienylacetamido)cephalosporanic acid 7-(α-amino-4-carboxymethylaminophenylacetamido)cephalosporanic acid with 1-(2-sulfaminoethyl)tetrazole-5-thiol disodium salt as described in the procedure of Example 5 followed by removal of the protective group and conversion of the trifluoroacetic acid salts to the free acids as described therein gives the following compounds of this invention:

7-(α-amino-4-hydroxyphenylacetamido)-3-[1-(2-sulfaminoethyl)tetrazol-5-ylthiomethyl]-3-cephem-4-carboxylic acid 7-(α-amino-4-formamidophenylacetamido)-3-[1-(2-sulfaminoethyl)tetrazol-5-ylthiomethyl]-3-cephem-4-carboxylic acid 7-(α-amino-3-formamidophenylacetamido)-3-[1-(2-sulfaminoethyl)tetrazol-5-ylthiomethyl]-3-cephem-4-carboxylic acid 7-(α-amino-4-ureidophenylacetamido)-3-[1-(2-sulfaminoethyl)tetrazol-5-ylthiomethyl]-3-cephem-4-carboxylic acid 7-(α-amino-3-ureidophenylacetamido-3-[1-(2-sulfaminoethyl)tetrazol-5-ylthiomethyl]-3-cephem-4-carboxylic acid 7-(α-amino-4-hydroxymethylphenylacetamido)-3-[1-(2-sulfaminoethyl)tetrazol-5-ylthiomethyl]-3-cephem-4-carboxylic acid 7-(α-amino-1,4-cyclohexadienylacetamido)-3-[1-(2-sulfaminoethyl)tetrazol-5-ylthiomethyl]-3-cephem-4-carboxylic acid 7-(α-amino-4-carboxymethylaminophenylacetamido)-3-[1-(2-sulfaminoethyl)tetrazol-5-ylthiomethyl]-3-cephem-4-carboxylic acid.

EXAMPLE 7

7-(4-Hydroxymandelamido)-3-[1-(2-sulfaminoethyl)tetrazol-5-ylthiomethyl]-3-cephem-4-carboxylic acid is prepared by reaction of 7-(4-hydroxymandelamido)-cephalosporanic acid sodium salt and 1-(2-sulfaminoethyl)tetrazole-5-thiol disodium salt followed by treatment of the product with Amberlite IR-120H ion exchange resin as described in the procedure of Example 1.

EXAMPLE 8

When the sodium salt of a cephalosporanic acid listed below:

7-(3-sydnoneacetamido)cephalosporanic acid
7-(2-aminomethylphenylacetamido)cephalosporanic acid is reacted with 1-(2-سulfaminoethyl)tetrazole-5-thiol disodium salt by the procedure described in Example 1 and the product is converted to the free acid as described therein, the following compounds of this invention are obtained, respectively:

7-(3-sydnoneacetamido)-3-[1-(2-sulfaminoethyl)tetrazol-5-ylthiomethyl]-3-cephem-4-carboxylic acid
7-(2-aminomethylphenylacetamido)-3-[1-(2-sulfaminoethyl)tetrazol-5-ylthiomethyl]-3-cephem-4-carboxylic acid.

EXAMPLE 9

Reaction of the sodium salt of a cephalosporanic acid listed below:

7-(2,2,2-trifluoroethylthioacetamido)cephalosporanic acid
7-methylthioacetamidocephalosporanic acid with 1-(2-sulfaminoethyl)tetrazole-5-thiol as described in the procedure of Example 4 gives, after conversion of the salts formed to the free acids, the following compounds of this invention as final products:

7-(2,2,2-trifluoroethylthioacetamido)-3-[1-(2-sulfaminoethyl)tetrazol-5-ylthiomethyl]-3-cephem-4-carboxylic acid
7-methylthioacetamido-3-[1-(2-sulfaminoethyl)tetrazol-5-ylthiomethyl]-3-cephem-4-carboxylic acid.

EXAMPLE 10

When an equivalent amount of an N-aminoalkylacetamide listed below:

N-(3-aminopropyl)acetamide
N-(4-aminobutyl)acetamide
N-(5-aminopentyl)acetamide is used in the procedure of Example 1 in place of N-(2-aminoethyl)acetamide and the resulting dithiocarbamates are treated with sodium azide to produce the corresponding 1-acetamidoalkyltetrazole-5-thiols which are converted to the 1-sulfaminoalkyl derivatives, all as described therein, the following 1-sulfaminoalkyltetrazole-5-thiols are obtained:

1-(3-sulfaminopropyl)tetrazole-5-thiol
1-(4-sulfaminobutyl)tetrazole-5-thiol
1-(5-sulfaminopentyl)tetrazole-5-thiol.

Reaction of the disodium salt of a 1-sulfaminoalkyltetrazole-5-thiol listed above with 7-D-mandelamidocephalosporanic acid sodium salt as described in the procedure of Example 1 followed by conversion of the salts formed to the free acids, gives the following compounds of this invention:

7-D-mandelamido-3-[1-(3-sulfaminopropyl)tetrazol-5-ylthiomethyl]-3-cephem-4-carboxylic acid
7-D-mandelamido-3-[1-(4-sulfaminobutyl)tetrazol-5-ylthiomethyl]-3-cephem-4-carboxylic acid
7-D-mandelamido-3-[1-(5-sulfaminopentyl)tetrazol-5-ylthiomethyl]-3-cephem-4-carboxylic acid.

Likewise, reaction of the substituted tetrazol thiols or the corresponding disodium salt listed above with any of the 7-acyl cephalosporanic acids mentioned herein or their corresponding salts according to procedures described herein gives the corresponding compounds of this invention.

EXAMPLE 11

Reaction of a cephalosporanic acid listed below or its corresponding salt:

7-(α-hydroxy-2-thienylacetamido)cephalosporanic acid
7-(α-carboxy-2-thienylacetamido)cephalosporanic acid
7-(α-sulfophenylacetamido)cephalosporanic acid with 1-(2-sulfaminoethyl)tetrazole-5-thiol disodium salt by procedures described hereinabove gives, after conversion of the product to the free acid, the following compounds of this invention:

7-(α-hydroxy-2-thienylacetamido)-3-[1-(2-sulfaminoethyl)tetrazol-5-ylthiomethyl]-3-cephem-4-carboxylic acid
7-(α-carboxy-2-thienylacetamido)-3-[1-(2-sulfaminoethyl)tetrazol-5-ylthiomethyl]-3-cephem-4-carboxylic acid
7-(α-sulfophenylacetamido)-3-[1-(2-sulfaminoethyl)tetrazol-5-ylthiomethyl]-3-cephem-4-carboxylic acid.

EXAMPLE 12

7-Amino-3-[1-(2-sulfaminoethyl)tetrazol-5-ylthiomethyl]-3-cephem-4-carboxylic acid To a mixture of 97 g (200 ml, 2.1 mol) of formic acid, distilled from anhydrous copper sulfate, and 37.5 ml (0.4 mol) of acetic anhydride was added 25.0 g (0.1 mol) of 7-aminocephalosporanic acid. The mixture was stirred at ambient temperature for 0.5 hour, then evaporated to dryness. The residue was dissolved in ethyl acetate and the ethyl acetate solution was filtered and evaporated to dryness to give a residue which was recrystallized from ether-petroleum ether to give 7-formamidocephalosporanic acid.

A mixture of 1.0 g (3.3 mmol) of 7-formamidocephalosporanic acid and 0.7 g (2.6 mmol) of 1-(2-sulfaminoethyl)tetrazole-5-thiol disodium salt in 15 ml of water is stirred at 65°–70° for 3 hours while maintaining the pH at 7.0. The mixture is cooled, acidified to pH 1.0 with hydrochloric acid and extracted with ethyl acetate. The extract is filtered and the filtrate is evaporated to dryness to give a residue which is dissolved in methanol. The methanol solution is filtered and ether is added to precipitate the title compound which is collected by filtration.

EXAMPLE 13

7-(4-Pyridylthioacetamido)-3-[1-(2-sulfaminoethyl)tetrazol-5-ylthiomethyl]-3-cephem-4-carboxylic acid (4-Pyridylthio)acetyl chloride (0.53 g, 2.8 mmol) is dropwise added to a mixture of 1.0 g of 7-amino-3-[1-(2-sulfaminoethyl)tetrazol-5-ylthiomethyl]-3-cephem-4-carboxylic acid and 0.9 g (9.0 mmol) of triethylamine in 10 ml of dry dimethylformamide. The reaction mixture is stirred for 1.5 hour at −10°, then it is warmed to ambient temperature and stirred for 1 hour. This mixture is filtered and the filtrate is diluted with 200 ml of ether-petroleum ether. The precipitate is collected by filtration to give the title compound.

EXAMPLE 14

Acylation of 7-amino-3-[1-(2-sulfaminoethyl)tetrazol-5-ylthiomethyl]-3-cephem-4-carboxylic acid with an activated derivative of the following acids:

cyanoacetic acid
3-pyridylthioacetic acid
cyanomethylthioacetic acid
2,2,2-trifluoroethylsulfinylacetic acid
methylsulfonylacetic acid
2-pyridone-N-acetic acid
4-pyridone-N-acetic acid as described in the procedure of Example 13 gives the following compounds of this invention:

7-cyanoacetamido-3-[1-(2-sulfaminoethyl)tetrazol-5-ylthiomethyl]-3-cephem-4-carboxylic acid
7-(3-pyridylthioacetamido)-3-[1-(2-sulfaminoethyl)tetrazol-5-ylthiomethyl]-3-cephem-4-carboxylic acid
7-cyanomethylthioacetamido-3-[1-(2-sulfaminoethyl)tetrazol-5-ylthiomethyl]-3-cephem-4-carboxylic acid
7-(2,2,2-trifluoroethylsulfinylacetamido)-3-[1-(2-sulfaminoethyl)tetrazol-5-ylthiomethyl]-3-cephem-4-carboxylic acid
7-methylsulfonylacetamido-3-[1-(2-sulfaminoethyl)tetrazol-5-ylthiomethyl]-3-cephem-4-carboxylic acid
7-(2-pyridoneacetamido)-3-[1-(2-sulfaminoethyl)tetrazol-5-ylthiomethyl]-3-cephem-4-carboxylic acid
7-(4-pyridoneacetamido)-3-[1-(2-sulfaminoethyl)tetrazol-5-ylthiomethyl]-3-cephem-4-carboxylic acid.

EXAMPLE 15

7-(D-α-Formyloxyphenylacetamido)-3-[1-(2-sulfaminoethyl)tetrazol-5-ylthiomethyl]-3-cephem-4-carboxylic acid 7-Amino-3-[1-(2-sulfaminoethyl)tetrazol-5-ylthiomethyl]-3-cephem-4-carboxylic acid is reacted with the formate ester of D-mandeloyl chloride according to the procedure of Example 13 to give the title compound.

EXAMPLE 16

7α-Methoxy-7β-(2-thienylacetamido)-3-[1-(2-sulfaminoethyl)tetrazol-5-ylthiomethyl]-3-cephem-4-carboxylic acid A solution of 1.28 g (3 mmol) of 7α-methoxy-7β-(2-thienylacetamido)cephalosporanic acid sodium salt is dissolved in 50 ml of water, 1.33 g (4.5 mmol) of 1-(2-sulfaminoethyl)tetrazole-5-thiol disodium salt is added and the solution is heated at 70° until thin layer chromatography indicates consumption of the starting material (ca. 5 hours). The reaction mixture is chromatographed on XAD-4 ion exchange resin with, after washing with water, methanol as eluant. Evaporation of the methanol solution gives the title compound as the disodium salt.

7α-Methoxy-7β-(2-thienylacetamido)-3-[1-(2-sulfaminoethyl)tetrazol-5-ylthiomethyl]-3-cephem-4-carboxylic acid disodium salt is converted to the title compound as described above.

EXAMPLE 17

7α-Methoxy-7β-trifluoromethylthioacetamido-3-[1-(2-sulfaminoethyl)tetrazol-5-ylthiomethyl]-3-cephem-4-carboxylic acid To a cold solution of 5.25 g (0.012 mol) of 7β-amino-7α-methoxycephalosporanic acid benzhydryl ester in 200 ml of methyl chloride containing 1.79 g (0.012 mol) of N,N-diethylaniline is added dropwise over a 20 minute period a solution of 1.82 g (0.012 mol) of trifluoromethylthioacetyl chloride in 50 ml of methylene chloride. After stirring for 30 minutes, the mixture is extracted successively with 5% aqueous sodium bicarbonate, 5% aqueous hydrochloric acid and finally with brine. The organic phase is dried (MgSO₄) and the solvent evaporated to give 7α-methoxy-7β-trifluoromethylthioacetamidocephalosporanic acid benzhydryl ester.

7α-Methoxy-7β-trifluoromethylthioacetamidocephalosporanic acid benzhydryl ester is dissolved in a cold mixture of trifluoroacetic acid-anisole (2:1) and the mixture is stirred for 1.5 hour without external cooling. The solvent is evaporated in vacuo and the residual product is taken up in ethyl acetate, washed with water, dried (MgSO₄) and concentrated in vacuo to a small volume. This solution is added dropwise to stirred petroleum ether to precipitate 7α-methoxy-7β-trifluoromethylthioacetamidocephalosporanic acid.

7α-Methoxy-7β-trifluoromethylthioacetamidocephalosporanic acid (2.2 g, 5 mmol) is suspended in 75 ml of water and 0.4 g of solid sodium bicarbonate is added until solution is complete. To this solution is added 2.21 g (7.5 mmol) of 1-(2-sulfaminoethyl)tetrazole-5-thiol disodium salt and the mixture is heated at 70° for 7 hours. The pH of the reaction mixture is maintained at 7.5 by dropwise addition of 3 N hydrochloric acid as necessary. Progress of the reaction is monitored by thin layer chromatography and judged to be complete when tlc indicates disappearance of starting material. The reaction mixture is chromatographed on a column of XAD-4 resin and the product is eluted from the column with methanol. Evaporation of the methanol solution gives 7α-methoxy-7β-trifluoromethylthioacetamido-3-[1-(2-sulfaminoethyl)tetrazol-5-ylthiomethyl]-3-cephem-4-carboxylic acid disodium salt.

The disodium salt is converted to the title compound by procedures described hereinabove.

EXAMPLE 18

7β-D-Mandelamido-7α-methoxy-3-[1-(2-sulfaminoethyl)tetrazol-5-ylthiomethyl]-3-cephem-4-carboxylic acid A cold solution of 2.6 g (6 mmol) of 7β-amino-7α-methoxycephalosporanic acid benzhydryl ester in 100 ml of methylene chloride containing 0.9 g (6 mmol) of N,N-diethylaniline is treated dropwise over a 15 minute period with a solution of 1.7 g (6 mmol) of D-O-dichloroacetylmandeloyl chloride in 25 ml of methylene chloride. The reaction mixture is allowed to come to room temperature with stirring and then is extracted successively with 5% aqueous sodium bicarbonate, 5% hydrochloric acid and brine. The organic phase is dried and evaporated in vacuo. The residue is dissolved in cold trifluoroacetic acid-anisole (2:1) and the mixture is stirred at ambient temperature for 1 hour. The mixture is evaporated in vacuo and the residue is dissolved in 5% aqueous sodium bicarbonate. The pH is raised to 9–9.3 by addition of 5% aqueous sodium carbonate and maintained there for 30 minutes to complete cleavage of the dichloroacetyl group. The solution is cooled in ice, layered with ethyl acetate and acidified to pH 2.0 with dilute hydrochloric acid. The layers are separated and after a second extraction of the aqueous layer with ethyl acetate the organic phases are combined, dried and evaporated in vacuo to yield 7β-D-mandelamido-7α-methoxycephalosporanic acid.

7β-D-Mandelamido-7α-methoxycephalosporanic acid (2.2 g, 5 mmol) is suspended in 75 ml of water and solid sodium bicarbonate is added until all of the acid has dissolved. To this is added 2.21 g (7.5 mmol) of 1-(2-sulfaminoethyl)tetrazole-5-thiol disodium salt and the mixture is heated at 70° for 7 hours. The pH of the reaction mixture is maintained at 7.5 by addition of 3 N hydrochloric acid. Chromatography of this solution on XAD-4 resin while eluting with methanol gives, upon evaporation of the methanol, the title compound as its disodium salt.

7β-D-Mandelamido-7α-methoxy-3-[1-(2-sulfaminoethyl)tetrazol-5-ylthiomethyl]-3-cephem-4-carboxylic acid disodium salt is converted to the title compound by procedures described hereinabove.

EXAMPLE 19

7α-Methoxy-7β-(D-α-aminophenylacetamido)-3-[1-(2-sulfaminoethyl)tetrazol-5-ylthiomethyl]-3-cephem-4-carboxylic acid To a solution of 5.3 g (0.012 mol) of 7β-amino-7α-methoxycephalosporanic acid p-nitrobenzyl ester in 200 ml of methylene chloride is added 3.0 g (0.012 mol) of D-α-t-butoxycarbonylaminophenylacetic acid and 2.5 g (0.012 mol) of dicyclohexylcarbodiimide. The mixture is stirred for 18 hours at ambient temperature then filtered. The filtrate is evaporated in vacuo and the residue is dissolved in methanol-tetrahydrofuran and hydrogenated over 5% palladium on carbon to give 7β-(D-α-t-butoxycarbonylaminophenylacetamido)-7α-methoxycephalosporanic acid.

7β-(D-α-t-Butoxycarbonylaminophenylacetamido)-7α-methoxycephalosporanic acid (2.68 g, 5 mmol) is dissolved in 75 ml of water by adding 0.4 g of solid sodium bicarbonate. 1-(2-Sulfaminoethyl)tetrazole-5-thiol disodium salt (2.21 g, 7.5 mmol) is added and the reaction mixture is heated at 70° until thin layer chromatography indicates that the starting material had disappeared. The reaction mixture is chromatographed on XAD-4 resin and eluted with methanol. Evaporation of the methanol solution gives 7α-methoxy-7β-(D-α-t-butoxycarbonylaminophenylacetamido)-3-[1-(2-sulfaminoethyl)tetrazol-5-ylthiomethyl]-3-cephem-4-carboxylic acid disodium salt.

The disodium salt is suspended in 1:1 trifluoroacetic acid-anisole and stirred at ambient temperature for two hours. Excess trifluoroacetic acid is removed by evaporation, the residue is triturated with ether and the resulting precipitate is collected by filtration and stirred with acetonitrile to give the title compound as its trifluoroacetic acid salt.

An aqueous solution of the trifluoroacetic acid salt is brought to pH 7 by addition of 5% aqueous sodium bicarbonate then chromatographed on XAD-4 resin with methanol as elutant. The solid material obtained after evaporation of the methanol is dissolved in water and the aqueous solution is passed through a cation exchange column (IR-12OH). Lyophilization of the eluted material gives the title compound.

EXAMPLE 20

7α-Methoxy-7β-(1-tetrazolylacetamido)-3-[1-(2-sulfaminoethyl)tetrazol-5-ylthiomethyl]-3-cephem-4-carboxylic acid Substitution of an equivalent amount of 1-tetrazolylacetyl chloride in the procedure of Example 17 gives 7α-methoxy-7β-(1-tetrazolylacetamido)cephalosporanic acid benzhydryl ester which is converted to 7α-methoxy-7β-(1-tetrazolylacetamido)cephalosporanic acid is described therein.

Reaction of 7α-methoxy-7β-(1-tetrazolylacetamido)-cephalosporanic acid, 1-(2-sulfaminoethyl)tetrazole-5-thiol disodium salt and sodium bicarbonate as described in Example 17 gives, after conversion of the product disodium salt to the free acid as described above, the title compound.

EXAMPLE 21

An injectable pharmaceutical composition is formed by adding sterile water or sterile saline solution (2 ml) to 500 mg of 7-D-mandelamido-3-[1-(2-sulfaminoethyl)tetrazol-5-ylthiomethyl]-3-cephem-4-carboxylic acid disodium salt.

Pharmaceutical compositions of the other antibacterial compounds disclosed above may be formulated in a similar manner.

What is claimed is:

1. A compound of the formula:

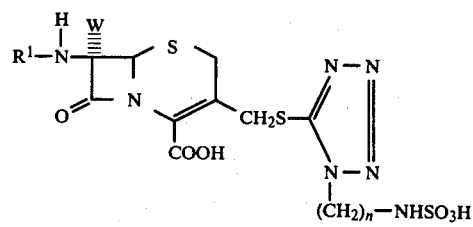

in which:

W is hydrogen or methoxy, $R^1$ is an acyl group of the formula:

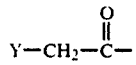

where:
Y is thienyl, tetrazolyl, sydnone, cyano or aminomethylphenyl; and
n is two to five,
or a non-toxic pharmaceutically acceptable salt thereof.

2. A compound according to claim 1 in which n is two.

3. A compound according to claim 1 in which Y is thienyl or tetrazolyl.

4. A compound according to claim 3 in which W is hydrogen.

5. A compound according to claim 3 in which W is methoxy.

6. A compound according to claim 4, said compound being 7-(2-thienylacetamido)-3-[1-(2-sulfaminoethyl)tetrazol-5-ylthiomethyl]-3-cephem-4-carboxylic acid.

7. A compound according to claim 4, said compound being 7-(1-tetrazolylacetamido)-3-[1-(2-sulfaminoethyl)tetrazol-5-ylthiomethyl]-3-cephem-4-carboxylic acid.

8. A compound according to claim 5, said compound being 7α-methoxy-7β-(2-thienylacetamido)-3-[1-(2-sulfaminoethyl)tetrazol-5-ylthiomethyl]-3-cephem-4-carboxylic acid.

9. A compound according to claim 5, said compound being 7α-methoxy-7β-(1-tetrazolylacetamido)-3-[1-(2-sulfaminoethyl)tetrazol-5-ylthiomethyl]-3-cephem-4-carboxylic acid.

10. An antibacterial pharmaceutical composition comprising a compound as claimed in claim 1 and a pharmaceutically acceptable carrier therefor.

11. An antibacterial pharmaceutical composition comprising a compound as claimed in claim 6 and a pharmaceutically acceptable carrier therefor.

12. A method of treating bacterial infections comprising administering internally by injection to an infected or susceptible warm-blooded animal as antibacterially effective but nontoxic dose of a compound as claimed in claim 1.

13. A compound according to claim 4, said compound being 7-(2-thienylacetamido)-3-[1-(2-sulfaminoethyl)tetrazol-5-ylthiomethyl]-3-cephem-4-carboxylic acid disodium salt.

14. A compound according to claim 4, said compound being 7-(1-tetrazolylacetamido)-3-[1-(2-sulfaminoethyl)tetrazol-5-ylthiomethyl]-3-cephem-4-carboxylic acid disodium salt.

15. An antibacterial pharmaceutical composition comprising a compound as claimed in claim 7 and a pharmaceutically acceptable carrier therefor.

16. An antibacterial pharmaceutical composition comprising a compound as claimed in claim 13 and a pharmaceutically acceptable carrier therefor.

17. An antibacterial pharmaceutical composition comprising a compound as claimed in claim 14 and a pharmaceutically acceptable carrier therefor.

18. A method as claimed in claim 12, in which the compound is 7-(2-thienylacetamido)-3-[1-(2-sulfaminoethyl)tetrazol-5-ylthiomethyl]-3-cephem-4-carboxylic acid.

19. A method as claimed in claim 12, in which the compound is 7-(1-tetrazolylacetamido)-3-[1-(2-sulfaminoethyl)tetrazol-5-ylthiomethyl]-3-cephem-4-carboxylic acid.

20. A method as claimed in claim 12, in which the compound is 7-(2-thienylacetamido)-3-[1-(2-sulfaminoethyl)tetrazol-5-ylthiomethyl]-3-cephem-4-carboxylic acid disodium salt.

21. A method as claimed in claim 12, in which the compound is 7-(1-tetrazolylacetamido)-3-[1-(2-sulfaminoethyl)tetrazol-5-ylthiomethyl]-3-cephem-4-carboxylic acid disodium salt.

* * * * *